United States Patent
Nguyen et al.

(10) Patent No.: US 6,518,074 B1
(45) Date of Patent: Feb. 11, 2003

(54) BACKSIDE IC DEVICE PREPARATION PROCESS

(75) Inventors: Hiep V. Nguyen, Santa Clara, CA (US); Henry Acedo, Morgan Hill, CA (US); Smith J. Johnson, Sunnyvale, CA (US); Kevin Weaver, San Jose, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 0 days.

(21) Appl. No.: 09/672,431

(22) Filed: Sep. 28, 2000

(51) Int. Cl.[7] .............................................. H01L 21/66
(52) U.S. Cl. ........................................ 438/14; 438/692
(58) Field of Search .............................. 438/459, 692, 438/928, 704, 305, 275, 279, 592, 14

(56) References Cited

U.S. PATENT DOCUMENTS

| | | | | |
|---|---|---|---|---|
| 4,284,072 A | * | 8/1981 | McKaveney | 126/661 |
| 4,980,019 A | * | 12/1990 | Baerg | 438/106 |
| 5,980,720 A | * | 11/1999 | Park et al. | 205/118 |
| 6,077,452 A | * | 6/2000 | Litvak | 216/85 |
| 6,080,675 A | * | 6/2000 | Prall et al. | 438/694 |
| 6,087,199 A | * | 7/2000 | Pogge et al. | 438/106 |
| 6,156,580 A | * | 12/2000 | Wooten et al. | 438/16 |
| 6,168,960 B1 | * | 1/2001 | Ii | 438/14 |
| 6,261,870 B1 | * | 7/2001 | Haehn et al. | 257/676 |
| 6,395,580 B1 | * | 5/2002 | Tseng | 438/108 |
| 6,403,439 B1 | * | 6/2002 | Lee | 438/14 |
| 6,428,718 B1 | * | 8/2002 | Birdsley et al. | 216/84 |

OTHER PUBLICATIONS

Zant, Peter Van, "Microchip Fabrication, a Practical Guide to Semiconductor Manufacturing", Apr. 3, 2000, McGraw hill, 4th Ed., pp. 63–65, 262, 270, 567–568, and 612.*

Zant, Peter Van, "Microchip Fabrication, A practical Guide to Semiconductor Manufacturing", 4th Ed., pp. 257–271.*

* cited by examiner

Primary Examiner—John F. Niebling
Assistant Examiner—Stacy A Whitmore
(74) Attorney, Agent, or Firm—Skjerven Morrill LLP

(57) ABSTRACT

An integrated circuit backside preparation process back-thins a die using a dry etch process. A wet etch process decaps the integrated circuit to expose the die. After polishing, the prepared integrated circuit is ready for a backside debug analysis.

11 Claims, 3 Drawing Sheets

| BACKSIDE SI ETCH | GAS STABILIZATION | UHF ON | SEND SF6 | SF6 RAMP | ETCH SI |
|---|---|---|---|---|---|
| AR | 100 SCCM | 100 SCCM | 100 SCCM | 100 SCCM | 90 SCCM |
| O2 | 0 SCCM | 0 SCCM | 0 SCCM | 0 SCCM | 0 SCCM |
| SF6/200 | 0 SCCM | 0 SCCM | 10 SCCM | 35 SCCM | 35 SCCM |
| SF6/25 | 0 SCCM | 0 SCCM | 0 SCCM | 0 SCCM | 0 SCCM |
| CF4 | 0 SCCM | 0 SCCM | 0 SCCM | 0 SCCM | 0 SCCM |
| CHF3 | 0 SCCM | 0 SCCM | 5 SCCM | 5 SCCM | 5 SCCM |
| C2F6 | 0 SCCM | 0 SCCM | 0 SCCM | 0 SCCM | 0 SCCM |
| HE | 20 SCCM | 20 SCCM | 20 SCCM | 20 SCCM | 20 SCCM |
| THROTTLE V. STAT | REGULATED | REGULATED | REGULATED | REGULATED | REGULATED |
| WORK PRESSURE | 100 MILLITORR | 100 MILLITORR | 100 MILLITORR | 45 MILLITORR | 45 MILLITORR |
| THROTTLE V. POS | 0 | 0 | 0 | 0 | 0 |
| CATHODE HEIGHT | 80 MM | 80 MM | 80 MM | 80 MM | 80 MM |
| RF STATUS | MANUAL | MANUAL | MANUAL | MANUAL | MANUAL |
| RF POWER | 0 WATTS | 0 WATTS | 0 WATTS | 0 WATTS | 0 WATTS |
| SELF BIAS | 0 VOLTS | 0 VOLTS | 0 VOLTS | 0 VOLTS | 0 VOLTS |
| LOAD | 320 | 320 | 320 | 320 | 320 |
| TUNE | 2350 | 2350 | 2350 | 2350 | 2350 |
| UHF POWER | 0 WATTS | 1400 WATTS | 1600 WATTS | 1800 WATTS | 1800 WATTS |
| CHILLER TEMP | 18 C | 18 C | 18 C | 18 C | 18 C |
| TIME | 20 SECONDS | 5 SECONDS | 5 SECONDS | 30 SECONDS | 3600 SECONDS |

FIG. 3

- 75 — Graphite shield for package protection during HDP RIE etch.
- 80 — Opening in shield for die exposure to plasma. Package is coated/masked with graphite paint here too.
- 70 — Backside of Si Die.

BACKSIDE IC DEVICE PREPARATION PROCESS

BACKGROUND

1. Field of the Invention

This invention relates to failure analysis of integrated circuit (IC) devices, and in particular, to an etch process for backside analysis.

2. Description of Related Art

The complexity of integrated circuits continues to increase as their dimensions decrease. The increased complexity drives up production costs, mandating efforts to limit the number of defective products. Despite the advance of technology, the wafer production process still has yields significantly less than 100%, making failure analysis an important tool for semiconductor manufacturers to limit the amount of defective product.

Numerous problems cause ICs to become defective. For example, minute dust particles can cause short circuits or open circuits, oxide can breakdown or be too thin, and metal can over-concentrate or under-concentrate in specific locations. A failure analysis typically starts by locating the site of the failure, a technique known as failure site isolation. This can be done electrically by using electrical test results to identify the failure location. Alternatively, physical methods can be employed to detect secondary effects of the failure such as identifying light emission or infra-red emission from the failure site. Another physical method employs probing techniques to access nodes or nets within the IC.

The aforementioned complexity of ICs has reduced the effectiveness of purely electrical methods, particularly for logic and analog circuits. Probing techniques also suffer from this complexity, e.g, from ICs having multiple layers of metallization making nodes inaccessible. In addition, modern packaging techniques-such as flip chip-make probing techniques problematic. Hence, backside physical analysis techniques have been developed, avoiding the top or active side of the die and the problems associated with purely electrical or probing techniques. For example, both infra-red and visible light emission (optical de-bug ) analyses as well as focused ion beam, optical beam induced current, and laser voltage probing techniques can be accomplished from the backside of the IC.

Regardless of the particular technique employed, a backside analysis will generally begin by using a milling machine to remove a backside portion of the IC, exposing the silicon substrate of the die used to form the IC. This silicon substrate is normally around 700 microns thick and must be thinned and then polished to permit light emissions to pass through what remains of the substrate. Silicon, however, is very hard and quite brittle, which complicates the back-thinning of the chip. Microscopic cracks introduced by the milling have a tendency to propagate. In addition, milling through the metal die paddle or through a metal heat shield tends to drive bits of metal into the silicon, which also causes cracking. These propagated cracks, affect the backside analysis, giving false or misleading results. As a result, the milling must be done very carefully, introducing substantial delay in a backside analysis. Milling through the epoxy packaging material introduces further delay because the epoxy is extremely tenacious and tends to foul the milling head.

Mechanical milling may be accomplished in one tool but generally requires multiple machine set-ups to accomplish a series of grinds. Initially, a rough grind through the epoxy packaging material and metallic heat shield (if applicable) uses a coarse grit having a 60 micron ($\mu$M) dimension. Because a silicon die is generally bonded directly to the metallic heat shield, as the milling head grinds through the heat shield, the coarse grit will often drive microscopic bits of metal into the die, generating cracks. As the milling bit grinds through the die, the grit dimension is reduced, until finally a 3 $\mu$M grit is used for the polishing stage. The multiple stages of grinding the die often introduces inclusions and cracks into the die, producing artifacts and false results in the ensuing backside optical analysis.

Accordingly, there is a need in the art for backside thinning processes which avoid the problems introduced by mechanical back-thinning of silicon substrates and milling of associated metallic packaging structures and packaging.

SUMMARY

In accordance with one aspect of the invention, a dry etch process substantially back-thins a die through an exposed backside surface. A wet etch process exposes the backside surface of the die. After the die has been dry etched, a conventional polishing step prepares the die for a backside debug analysis.

The invention will be more fully understood upon consideration of the detailed description below, taken together with the accompanying drawings.

BRIEF DESCRIPTION OF THE DRAWINGS

FIG. 3 is a table of the operating parameters for a high density plasma reactive ion etch according to one embodiment of the invention.

Use of the same reference symbols in different figures indicates similar or identical items.

DETAILED DESCRIPTION OF THE PREFERRED EMBODIMENTS

Figure 1:
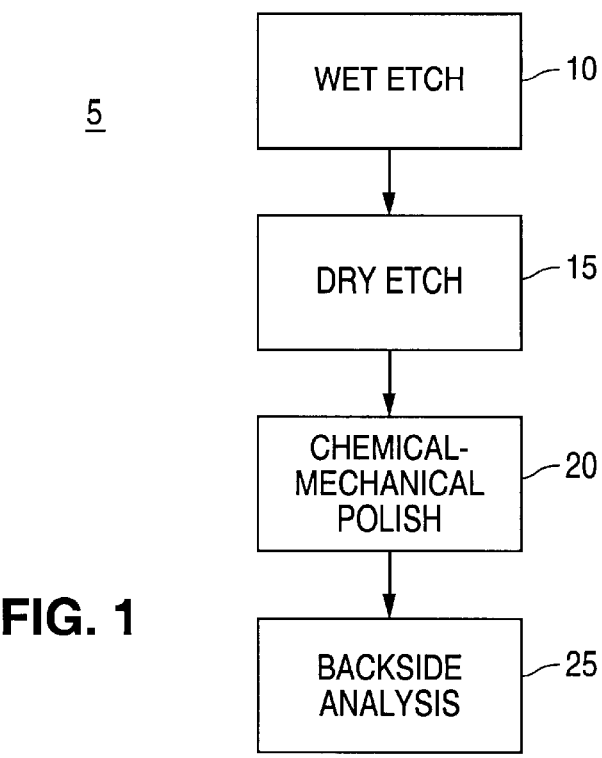
FIG. 1 is a flowchart for a backside preparation process according to one embodiment of the invention.

Referring now to the drawings, FIG. 1 illustrates a backside preparation process 5. The process 5 begins with a wet etch 10 to "decap" or uncover the IC, i.e., remove the packaging material and any metallic components such as a heat shield or die paddle from the backside of the die. Having exposed the die backside, the process 5 proceeds with a dry etch 15 of the die to substantially thin the die. For example, a preferred dry etch will thin the die substrate from its starting thickness (generally around 700 $\mu$M) to approximately 100 to 150 $\mu$M. Because the dry etch 15 generally leaves a roughened surface unsuitable for an optical analysis, the process 5 continues with a chemical-mechanical polish to thin the die substrate to be approximately 50 to 20 $\mu$M in thickness. At this stage, the die is ready for an optical debug analysis 25 using, for example, an automatic test equipment (ATE) or bench test set-up.

It will be appreciated that the process 5 may be subject to modifications that are within the scope of the invention. For example, rather than using a wet etch process to expose the backside of the die, a conventional mechanical milling machine could be used to expose the die. Although such a modification would be subject to the delay and problems associated with mechanically milling through the epoxy packaging material and any associated metal material, it would still benefit from the advantages associated with substantially thinning the exposed die with a dry etch process.

Figure 2:
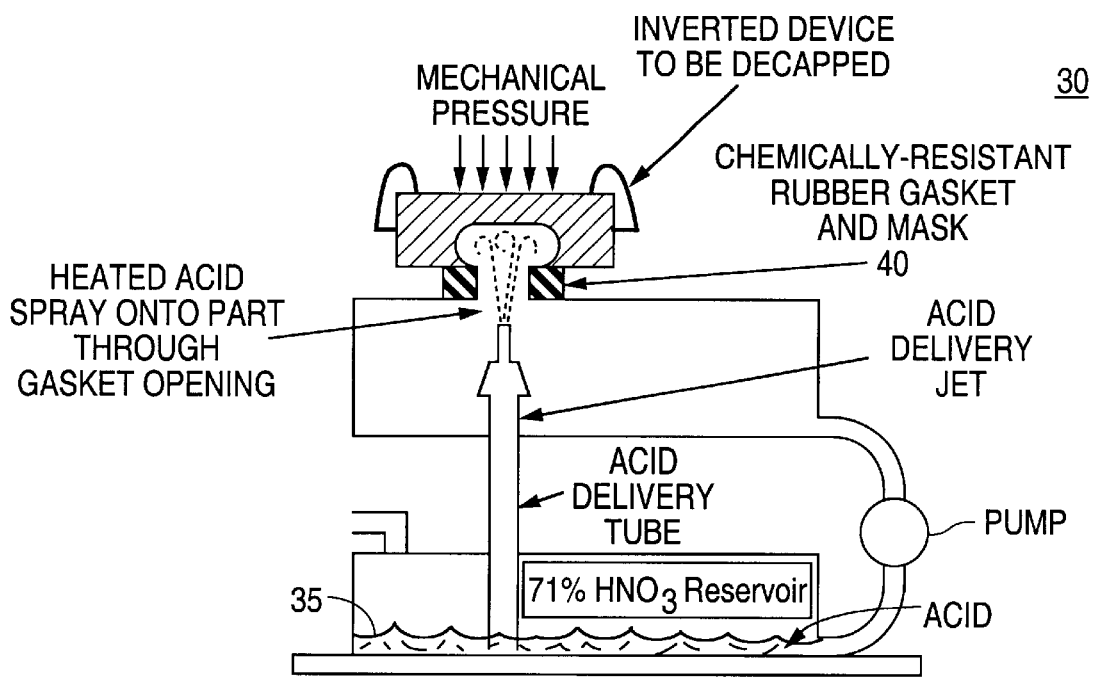
FIG. 2 is a cross-sectional view of a wet etch spray station for exposing the backside of the die.

The processes of FIG. 1 will now be discussed in greater detail, beginning with the wet etch process. FIG. 2 illustrates a wet etch spray station 30 for exposing the backside of the die. The spray station 35 has a reservoir 35 of etching solution suitable for decapping a packaged die, e.g., 71% $HNO_3$ solution. The spray station 35 pumps a heated spray of the etching solution onto the IC device. To prevent the etching solution from exposing leads and thus possibly affecting the electrical characteristics of the device, a chemically-resistant gasket and mask 40 masks the IC so that the etching occurs only over the active die surface. The IC is kept biased against the gasket and mask 40 to prevent leaks.

The etching solution may be varied depending upon the characteristics of the IC to be decapped. For example, should the IC not have a metallic heat shield or die paddle shielding the backside of the die, a 90% $HNO_3$ solution may be used to etch an epoxy packaging material. In addition, other suitable etching solutions include sulfuric acid. Regardless of the individual etching solution employed, a wet etch process to expose the backside of the die avoids the delay introduced by milling through the packaging material, which can often clog the milling bit. The wet etch process also avoids grinding bits of metal from heat shields, if present, into the die.

With the backside of the die exposed, a dry etch process may be performed to back-thin the die. Before the dry etch, the decapped IC may be rinsed with de-ionized water and dried with nitrogen gas to remove the wet etch solution and its by-products. Suitable dry etch processes include plasma etch and high density plasma reactive ion etch (HDP RIE) techniques. The inventors have discovered that an HDP RIE process using sulfur hexafluoride ($SF_6$) is particularly suitable, producing controllable etch rates of the die's silicon substrate. The etch rate increases with the applied power, however, so does the amount of roughness imparted on the etched surface. Thus, the applied power represents a compromise between a desired etching speed and an undesired roughness. One suitable compromise is given at an etch rate of 10 $\mu$M per minute. FIG. 3 is a table of the appropriate operating parameters for this particular HDP RIE etch rate. The dry etch process is preferably continued until a die thickness of approximately 50 to 20 $\mu$M is achieved.

Figure 4:
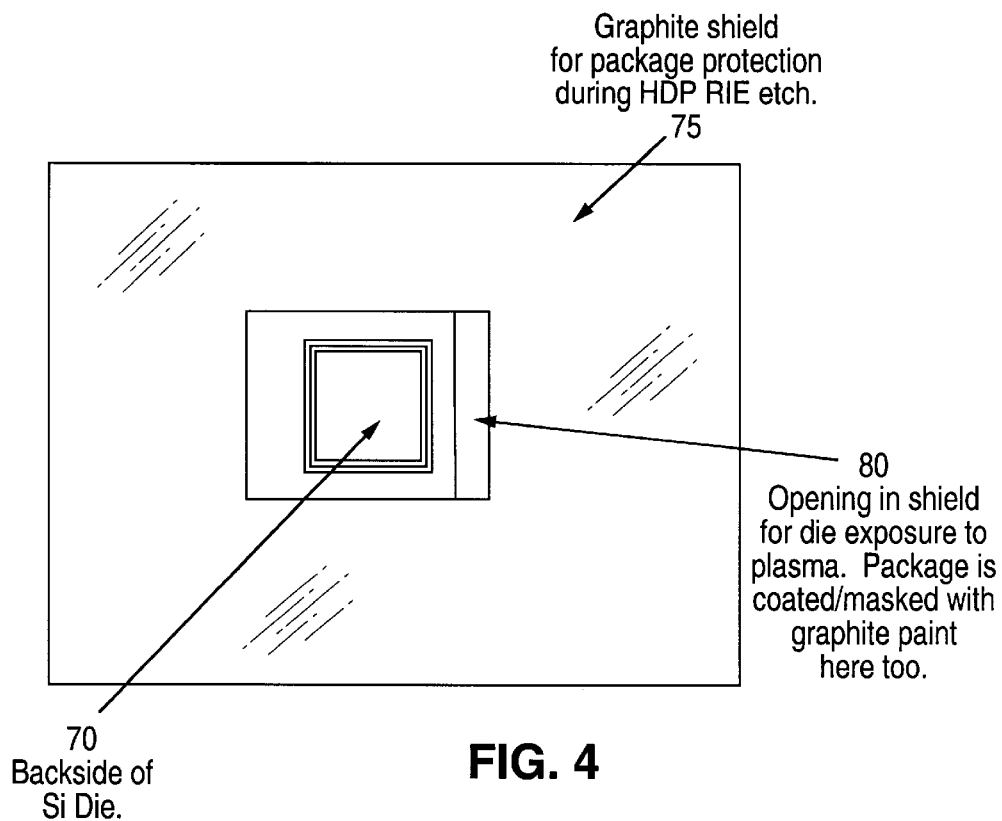
FIG. 4 illustrates a die backside having a mask for protection during a dry etch process.

Because dry etch processes can "redistribute" metal, the backside of the die may be masked with an appropriate shield before the dry etch process to prevent the exposure of metallic parts such as leads in the IC package. Redistribution of metal occurs when the metal is ionized but then deposits back down on the surface being etched. This deposit then acts as a mask, protecting the surface it covers from further etching, forming tenacious structures denoted as "grass." FIG. 4 illustrates a die 7 having a graphite shield 75 to protect the package components during an HDP RIE etch from such redistribution effects. The shield 75 has an opening to allow the exposed backside of the die 70 to be etched. To provide further protection, the package material at the edge of the die 70 may be coated or masked with a layer of graphite paint 80.

Figure 5:
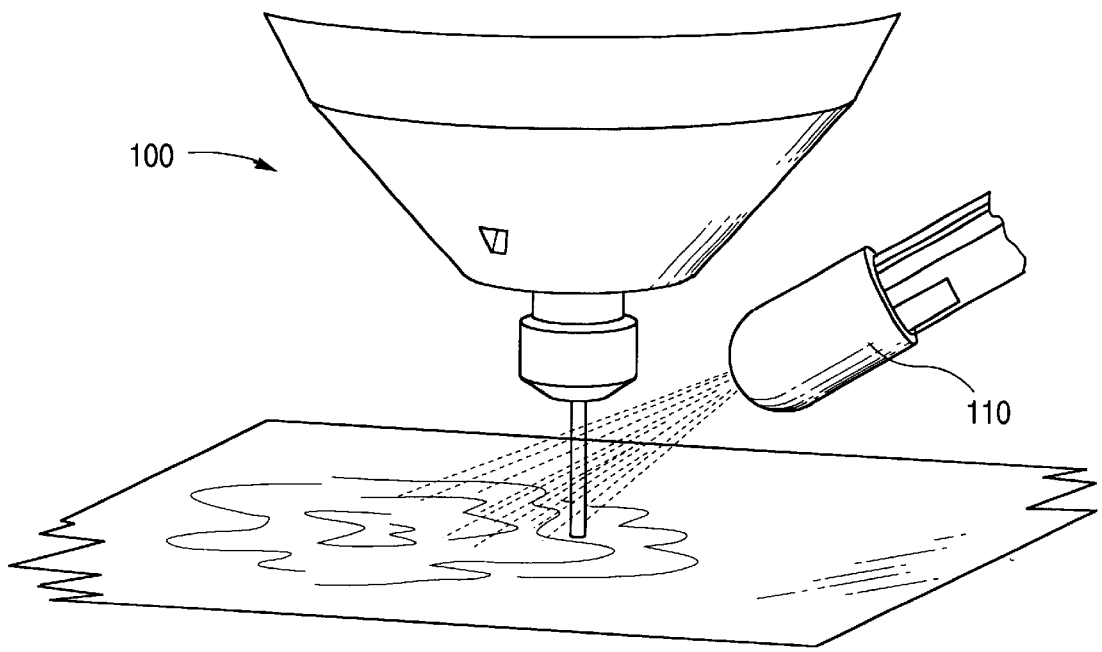
FIG. 5 illustrates a milling bit with a jet slurry for polishing a dry-etched die.

To provide a finish suitable for an optical backside analysis, the back-thinned die resulting from the dry etch process may be given a chemical-mechanical polish, using a conventional milling bit 100 as shown in FIG. 5. A jet of high pH slurry 110 provides a chemically active grit for generating a mirror finish. The grit dimensions will depend upon the amount of roughness imparted by the dry etch, with rougher surfaces needing a larger grit. The 10 $\mu$M per minute etch rate given by the operating parameters of FIG. 3 leaves a relatively smooth surface such that a grit of 0.05 $\mu$M is adequate. Alternatively, a rough polish could start with a grit dimension of 3.0 $\mu$M, followed by a fine polish with the 0.05 $\mu$M dimension grit. The polishing reduces the die thickness to be between approximately 50 to 20 $\mu$M. Although a high pH slurry is preferred for polishing, a purely mechanical slurry could also be used.

After rinsing with de-ionized water and drying with nitrogen gas, the IC device is ready for a backside analysis. Typical backside analyses include optical or infra-red emission microscopy, focused ion beam (FIB) probing techniques, and others.

Although the invention has been described with reference to particular embodiments, the description is only an example of the invention's application and should not be taken as a limitation. For example, the amount of die material removed during the dry etch process may be varied considerably. In addition, backside techniques such as FIB probing that do not require a polished backside surface can omit the polishing process. Consequently, various adaptations and combinations of features of the embodiments disclosed are within the scope of the invention as defined by the following claims.

We claim:

1. A process for preparing an integrated circuit, comprising:
    providing the integrated circuit including a package holding a die and a metallic component, the die having an active surface and an opposing backside surface, the metallic component being disposed between the die backside surface and the package;
    wet etching the integrated circuit package and metallic component to at least partially expose the backside surface of the die; and
    dry etching the exposed backside surface thereby to thin the die.
2. The process of claim 1, further comprising:
    polishing the dry etched backside die surface.
3. The process of claim 1, wherein the dry etching comprises high density reactive ion etching.
4. The process of claim 1, wherein the wet etching uses an $HNO_3$ solution.
5. The process of claim 1, wherein the wet etching uses a sulfuric acid solution.
6. The process of claim 1, wherein the dry etching thins the die to a thickness of approximately 100 to 150 $\mu$m.
7. The process of claim 2, wherein the polishing polishes the die to a thickness of approximately 20 to 50 $\mu$m.
8. The process of claim 1, further comprising prior to the dry etching:
    masking the exposed backside surface of the die with a material resistant to the dry etching.
9. The process of claim 8, wherein the material resistant to the dry etching comprises graphite.
10. The process of claim 8, wherein the masking comprises:
    painting a border of the package surrounding the exposed backside surface of the die with a graphite paint.
11. The process of claim 1, wherein the integrated circuit package has an exterior adjacent the backside surface of the die, the process further comprising:
    masking the exterior surface of the integrated circuit package with a material resistant to the wet etching.

* * * * *